United States Patent
Warawdekar et al.

(10) Patent No.: US 10,370,516 B2
(45) Date of Patent: Aug. 6, 2019

(54) BIO BASED PLASTICIZER WITH IMPROVED PROPERTIES AND PROCESSING CHARACTERISTICS OF POLYMER

(71) Applicant: FINE ORGANICS INDUSTRIES PVT LTD., Mumbai (IN)

(72) Inventors: Mayukh Warawdekar, Navi Mumbai (IN); Digambar Chavan, Navi Mumbai (IN)

(73) Assignee: Fine Organics Industries Pvt Ltd., Mumbai (IN)

(*) Notice: Subject to any disclaimer, the term of this patent is extended or adjusted under 35 U.S.C. 154(b) by 0 days.

(21) Appl. No.: 15/552,202

(22) PCT Filed: Feb. 19, 2016

(86) PCT No.: PCT/IN2016/000046
§ 371 (c)(1),
(2) Date: Aug. 18, 2017

(87) PCT Pub. No.: WO2016/132381
PCT Pub. Date: Aug. 25, 2016

(65) Prior Publication Data
US 2018/0037719 A1    Feb. 8, 2018

(30) Foreign Application Priority Data
Feb. 19, 2015    (IN) .......................... 537/MUM/2015

(51) Int. Cl.
*C08K 5/103* (2006.01)
*C08L 27/06* (2006.01)
*C07C 69/30* (2006.01)

(52) U.S. Cl.
CPC .............. *C08K 5/103* (2013.01); *C07C 69/30* (2013.01); *C08L 27/06* (2013.01)

(58) Field of Classification Search
CPC ........ C08K 5/103; C08K 5/101; C07C 69/30; C08L 27/06
See application file for complete search history.

(56) References Cited

U.S. PATENT DOCUMENTS

| | | | | |
|---|---|---|---|---|
| 4,426,477 A | * | 1/1984 | Yasumatsu | C08K 5/103 523/100 |
| 4,766,167 A | * | 8/1988 | Marnett | C08G 18/3221 524/310 |
| 6,734,241 B1 | * | 5/2004 | Nielsen | C08K 5/103 524/287 |
| 2003/0065073 A1 | * | 4/2003 | Lee | C08K 5/103 524/311 |
| 2011/0021680 A1 | * | 1/2011 | Colle | C07B 41/12 524/313 |

FOREIGN PATENT DOCUMENTS

| | | | | |
|---|---|---|---|---|
| JP | 2001151969 | * | 6/2001 | C08K 5/103 |
| KR | 100852295 | * | 8/2008 | C08K 3/40 |

OTHER PUBLICATIONS

JP 2001151969, Riken Vinyl IND, Vinyl Chloride Resin Composition for Sol, English translation, 10 pages (Year: 2001).*
KR 100852295, Itoh Katsumi, Inorganic particle-containing composition, transfer film and plasma display panel production process, English translation, 20 pages (Year: 2008).*
Vieira, M, G.A., et al., Natural-based plasticizers and biopolymer films: A review, 2011, European Polymer Journal, vol. 47; pp. 254-263 (Year: 2011).*
International Search Report issued in International patent application No. PCT/IN2016/000046, dated Jul. 14, 2016.

* cited by examiner

*Primary Examiner* — Yate' K Cutliff
(74) *Attorney, Agent, or Firm* — Seyfarth Shaw LLP

(57) ABSTRACT

A bio based plasticizer with improved properties and processing characteristics of polymer comprising at least 95% by weight compound of formula 1, [Formula should be inserted here] wherein $R_1$ $R_2$ and $R_3$ represent each an acyl group or a hydrogen atom, said acyl group comprises at least one with 2 carbon atoms and one with 12 carbon atoms, the acyl group having 2 carbon atoms is present in an amount, on an average, of up to 2 mole per mole of glycerine.

Compound of formula I

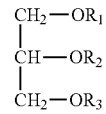

6 Claims, No Drawings

BIO BASED PLASTICIZER WITH IMPROVED PROPERTIES AND PROCESSING CHARACTERISTICS OF POLYMER

CROSS REFERENCES TO RELATED APPLICATIONS

This application is a U.S. National Stage application of PCT International Patent Application Number PCT/IN2016/000046, filed on Feb. 19, 2016, which claims priority to Indian Patent Application No. 537/MUM/2015, which was filed on Feb. 19, 2015 the disclosures of all of which is incorporated are hereby incorporated by reference in its entirety.

TECHNICAL FIELD

The present invention relates to a bio based plasticizer with improved properties and processing characteristics useful in the polymer industry.

BACKGROUND OF THE INVENTION

There are more than hundred commercially available primary plasticizers for polyvinylchloride. The polyvinylchloride plasticizer must act as a solvent for the crystalline part of the polyvinylchloride at flexible processing temperatures but not at lower temperatures. The plasticizer must not react with polyvinylchloride. The plasticizers are mainly esters. Phthalates are widely used in plastics and rubber around the world, but in the late nineties health issues such as abnormalities in physiological development were noticed. Thus; phthalate-free articles are mandatory for medical devices, toys, child-care articles and food packaging.

U.S. Pat. No. 2,615,159 (referred to herein as '159 patent, assigned to M/s The Procter & Gamble Company) discloses preparation of 1-stearyl-2,3-diacetin as a novel waxy, stable, translucent solid and similar compounds for use in food preparations such as candy coating.

U.S. Pat. No. 3,748,265 (referred to herein as '265 patent, assigned to M/s Dynamit Nobel Aktiengesellschaft) teaches preparation of oxidation resistant diacetyl monododecanoyl triglyceride and its mixtures with diacetyl monotetradecanoyl or diacetyl monohexadecanoyl triglycerides. The '265 patent does not teach bio based plasticizer with improved properties and/or processing characteristics.

European patent no. 1624014B1 (referred to herein as '014 patent, assigned to M/s Danisco A/S) relates to a process for the preparation of a novel plasticizer, compound of formula

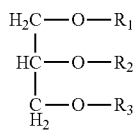

wherein at least one of $R_1$, $R_2$ and $R_3$ is a branched chain acyl group with a hydrophilic branch group wherein the hydrophilic branch group is an acyl group or a derivative thereof.

Polymer Testing 32 (2013) 272-278 suggests use of vegetable based plasticizer, fully acetylated glycerol monoester based on coconut oil (Acetem) comprising a mixture of caprylic ($C_8$), capric ($C_{10}$) and lauric acid ($C_{12}$) when used in polyvinylchloride films showed better mechanical performance and high transparency.

U.S. Pat. No. 4,426,477 (referred to herein as '477 patent, assigned to M/s Riken Vitamin Co. Ltd.) teaches use of a mixture of glycerin diacetate mono $C_{10-14}$ fatty acid content as a plasticizer in PVC.

All the above publications do not suggest improved properties of plasticizer such as substitution factor, plasticizing efficiency or overall migration. Further, there is no suggestion of improvement in processing characteristics such as hardness, flexibility at lower temperature, fusion time or torque which play an important role in polymer processing.

Several alternatives of vegetable origin based plasticizers have been developed with the view to substitute phthalates. In view of the same we have developed a bio based plasticizer with improved properties and processing characteristic which enables ease in polymer processing.

OBJECT OF THE INVENTION

The object of the present invention is to provide an environmental friendly plasticizer with improved properties and characteristics which aids polymer processing.

SUMMARY OF THE INVENTION

A bio based plasticizer with improved properties for polymer application(s) comprising at least 95% by weight compound of formula I,

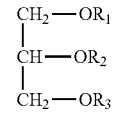

Compound of formula I wherein $R_1$, $R_2$ and $R_3$ represent each an acyl group or a hydrogen atom, said acyl group comprises at least one with 2 carbon atoms and one with 12 carbon atoms, the acyl group having 2 carbon atoms is present in an amount, on an average, of up to 2 mole per mole of glycerine; wherein the improved properties are plasticizing efficiency and/or substitution factor and/or overall migration and the polymer is selected from polyvinylchloride, polyvinylacetate, polyamide and rubber.

A bio based plasticizer for improving processing characteristics of polymer comprising at least 95% by weight compound of formula I,

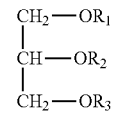

Compound of formula I wherein $R_1$, $R_2$ and $R_3$ represent each an acyl group or a hydrogen atom, said acyl group comprises one having 2 carbon atoms and one consisting mainly of those having 12 carbon atoms, the acyl group having 2 carbon atoms is present in an amount, on an average, of up to 2 mol per mol of glycerine; wherein the processing characteristics of polymer are tensile strength mechanical properties, degradation, flexibility at lower temperature, heat stability, rheological properties and hardness; and the polymer is selected from polyvinylchloride, polyvinylacetate, polyamide and rubber.

DESCRIPTION OF THE INVENTION

In our endeavor to prepare plasticizers which do not generate health hazard we have found a primary bio based plasticizer, compound of formula I, which is phthalate-free and non-toxic with superior plasticizing efficiency.

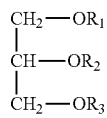

Compound of formula I

The bio based plasticizer of the present invention being non-toxic and edible can be used as a plasticizer for packaging materials in direct contact with food like packaging films, molded containers, for medical appliances and toys.

The bio based plasticizer of the present invention is accepted also as a food additive and can be used in the polymeric resin.

According to the first embodiment of the present invention is a bio based plasticizer with improved properties for polymer application(s) comprising at least 95% by weight compound of formula I,

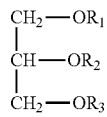

Compound of formula I wherein $R_1$, $R_2$ and $R_3$ represent each an acyl group or a hydrogen atom, said acyl group comprises at least one with 2 carbon atoms and one with 12 carbon atoms, the acyl group having 2 carbon atoms is present in an amount, on an average, of up to 2 mole per mole of glycerine; wherein the improved properties are plasticizing efficiency and/or substitution factor and/or overall migration and the polymer is selected from polyvinylchloride, polyvinylacetate, polyamide and rubber.

The concentration of the bio based plasticizer of the present invention used in the polymer may be selected from 20 to 60 phr.

Different properties of a plasticizer which are considered during selection of the plasticizer are plasticizing efficiency, substitution factor and overall migration.

The plasticizing efficiency of a plasticizer is measured by means of its glass transition temperature. The plasticizing efficiency of the bio based plasticizer of the present invention is improved by 5 to 10° C. drop glass transition temperature.

The substitution factor of the bio based plasticizer of the present invention is less than 1.0 when compared with dioctylphthalate (DOP).

The overall migration of the bio based plasticizer of the present invention is decreased by at least 1.5 times in polyvinylchloride as compared with dioctylphthalate in 3% aqueous solution of acetic acid.

According to another embodiment of the present invention is a bio based plasticizer with improved processing characteristics of polymer comprising at least 95% by weight compound of formula I,

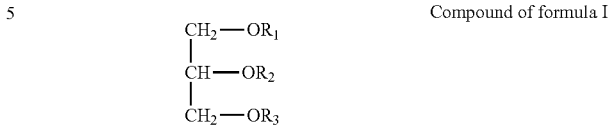

wherein $R_1$, $R_2$ and $R_3$ represent each an acyl group or a hydrogen atom, said acyl group comprises at least one with 2 carbon atoms and one with 12 carbon atoms, the acyl group having 0.2 carbon atoms is present in an amount, on an average, of up to 2 mole per mole of glycerine; wherein the processing characteristics of polymer are tensile strength mechanical properties, degradation, flexibility at lower temperature, heat stability, rheological properties and hardness; and the polymer is selected from polyvinylchloride, polyvinylacetate, polyamide and rubber.

The concentration of the bio based plasticizer of the present invention used in the polymer may be selected from 20 to 60 phr.

Mechanical properties of the polymer comprising bio based plasticizer of the present invention may be improved such as hardness by at least 5 to 10% when compared with polymer comprising diisononylcyclohexane 1,2 dicarboxylic ester (DINCH) in hardness test at 30 sec @40 phr.

Heat stability viz. static and dynamic of the polymer such as polyvinylchloride comprising bio based plasticizer, compound of formula I, is improved by at least 40% when compared with DOP by yellowness index @ASTM D1925 after 60 minutes.

Flexibility at lower temperature of the polymer comprising bio based plasticizer of the present invention is improved by at least 75% when compared with DOP measured by ASTM D 2137A.

The rheological properties of the polymer comprising bio based plasticizer of the present invention are also improved when compared with DOP or DINCH.

According to yet another embodiment is a thermoplastic resin composition obtained by blending the polymer bio based plasticizer, compound of formula I, with a polymeric resin.

The polymer may be selected from polyvinylchloride, polyvinylacetate, polyamide and rubber.

The compound of formula I may be prepared by methods known in the art such as reacting glycerine with lauric acid to obtain a mixture of mono, di and tri lauryl esters followed by purification and acetylation.

Definition of Terms

Glass transition temperature (Tg) is defined as the temperature at which the mechanical properties of a polymer radically change due to the internal movement of the polymer chains that form the polymer. At this temp the polymer become glassy to rubbery.

Substitution Factor

It is the ratio of phr of plasticizer required to get the same hardness as dioctylphthalate.

Overall Migration

Extraction of plasticizer from polymer

Hardness

The resistance of polymer to compression and indentation.

Static and Dynamic Heat Stability

Static heat stability is the stability of polymer exposed to temperature at (170-180) ° C. for 1 hour and observe the colour visually or by spectro photometer. Dynamic heat stability is the heat stability in two-roll-mill i.e. with heat and shear at processing temperature (180-200)° C.

Flexibility at Low Temperature

The temperature at which the material becomes brittle from flexible. If the low-temperature flexibility is better, the material will still be flexible even at lower temperature.

Fusion Time and Fusion Torque When Polymer compound is mixed under appropriate conditions of heat and shear, a fused mass is produced. This mass has certain melt characteristics which can be defined with a torque rheometer operated under fixed conditions of shear and temperature. Fusion time is the time required to get a molten mass at a certain temperature and shear with the fixed mass. Fusion torque is the Torque at this point i.e. at Fusion Time.

Tensile Strength: Ultimate tensile strength (UTS), often shortened to tensile strength (TS) is the maximum stress that a material can withstand while being stretched or pulled before failing or breaking. Tensile strength is the longitudinal stress required to break a prescribed specimen divided by the original cross-sectional area at the point of rupture within the gauge boundaries sustained by the specimen during the test.

The following examples illustrate preferred embodiments in accordance with the present invention without limiting the scope of the invention.

EXAMPLES

Example 1: Test Formulations

|  | A | B | C |
|---|---|---|---|
| PVC (K-67) | 100.0 | 100.0 | 100.0 |
| Ca/Zn stabilizer | 2.0 | 2.0 | 2.0 |
| Finawax-C | 0.4 | 0.4 | 0.4 |
| Epoxidised soyabean oil | 1.5 | 1.5 | 1.5 |
| DOP (DEHP) | 40.0 | — | — |
| Compound of formula I | — | 40.0 | — |
| 1,2 cyclohexane dicarboxylic acid, di-isononylester (DINCH) | — | — | 40.0 |

Example 2: Comparison of Glass Transition Temperature ASTM-D 3418

|  | 10 phr plasticizer | 20 phr plasticizer | 30 phr plasticizer | 40 phr plasticizer |
|---|---|---|---|---|
| A | 50 | 32 | 20 | 17 |
| B | 48 | 29 | 15 | 7 |
| C | 52 | 35 | 24 | 21 |

Example 3: Comparison of Substitution Factor (SF) Quantified as a Function of PVC Durometer Hardness

|  | Substitution factor @ 40 phr |
|---|---|
| A | 1.0 |
| B | 0.9 |
| C | 1.2 |

Example 4: Comparison of Overall Migration IS: 9845-1998

|  | mg/kg of PVC sheet @ 40 phr |
|---|---|
| A | 28.4 |
| B | 17.6 |
| C | NA |

Example 5: Comparison of Hardness ASTM-D-2240

|  | Hardness at 30 sec @ 40 phr |
|---|---|
| A | 78 |
| B | 77 |
| C | 83 |

Example 6: Comparison of Static and Dynamic Heat Stability

Static Heat Stability: Yellowness Index @ASTM D 1925 with Spectrometer SS 5100 R

| min | A | B | C |
|---|---|---|---|
| 0 | 11.0 | 10.2 | 15.0 |
| 10 | 15.5 | 15.2 | 20.6 |
| 20 | 16.0 | 17.2 | 41.4 |
| 30 | 28.0 | 21.0 | 67.1 |
| 40 | 42.2 | 26.0 | 87.4 |
| 50 | 55.2 | 30.2 | 98.8 |
| 60 | 67.7 | 39.7 | 109.7 |

Dynamic Heat Stability: Inhouse Method

|  | TRM Stability, min @170° C. | | |
|---|---|---|---|
|  | 50 | >60 | 40 |
| Yellowness Index | A | B | C |
| 0 min | 19.8 | 17.0 | 16.7 |
| 20 min | 50.0 | 64.1 | 80.6 |
| 30 min | 106.8 | 93.3 | 110.5 |

Example 7: Comparison of Low Temperature Brittleness Point c 40 Phr (ASTM D2137A)

|  | Temperature ° C. |
|---|---|
| A | −18 |
| B | −32 |
| C | −25 |

Example 8: Comparison of Fusion Time and Torque (in-House Method with Haake Rheometer)

| Haake conditions | @150° C./40 rpm/70 gm/15 min | |
|---|---|---|
| | Fusion time | Equilibrium torque, Nm, 15 min |
| A | 2.84 | 7.70 |
| B | 1.75 | 7.60 |
| C | 3.80 | 8.00 |

Example 9: Comparison of Degradation Time (in-House Method Using Haake Rheometer)

| Haake conditions | @180° C./40 rpm/70 gm |
|---|---|
| A | 25.8 |
| B | 26.8 |
| C | 24.0 |

We claim:

1. A polymer comprising a bio-based plasticizer at a concentration of 20 phr to 60 phr, wherein the bio-based plasticizer comprises at least 95% by weight compound of formula I,

formula I wherein $R_1$, $R_2$ and $R_3$ represent each an acyl group or a hydrogen atom, wherein the acyl group comprises at least one with 2 carbon atoms and one with 12 carbon atoms.

2. The polymer according to claim 1, wherein the concentration of the plasticizer is 30 phr to 60 phr.

3. The polymer according to claim 1, wherein the concentration of the plasticizer is 40 phr to 60 phr.

4. The polymer according to claim 1, wherein the polymer is selected from the group consisting of polyvinylchloride, polyvinylacetate, polyamide, and rubber.

5. The polymer according to claim 1, wherein the bio based plasticizer is with improved properties for polymer application(s) selected from the group consisting of plasticizing efficiency and/or substitution factor and/or overall migration.

6. The polymer according to claim 1, wherein the bio based plasticizer improves processing characteristics of polymer selected from the group consisting of tensile strength mechanical properties, degradation, flexibility at lower temperature, heat stability, rheological properties and hardness.

* * * * *